(12) United States Patent
Quaderer et al.

(10) Patent No.: US 10,656,133 B2
(45) Date of Patent: May 19, 2020

(54) CONTROLLING PLANT DETECTION SYSTEMS USING PHASE DELAY ANALYSIS

(71) Applicant: Trimble Inc., Sunnyvale, CA (US)

(72) Inventors: James G. Quaderer, Sunnyvale, CA (US); Aubrey Jason Calder, Mountain View, CA (US); Xin Zhao, San Jose, CA (US)

(73) Assignee: Trimble Inc., Sunnyvale, CA (US)

( * ) Notice: Subject to any disclaimer, the term of this patent is extended or adjusted under 35 U.S.C. 154(b) by 21 days.

(21) Appl. No.: 16/165,344

(22) Filed: Oct. 19, 2018

(65) Prior Publication Data

US 2020/0128639 A1  Apr. 23, 2020

(51) Int. Cl.
| | | |
|---|---|---|
| *G01N 33/00* | (2006.01) | |
| *G01N 21/25* | (2006.01) | |
| *G01J 9/00* | (2006.01) | |
| *A01M 21/00* | (2006.01) | |
| *H05B 45/10* | (2020.01) | |

(52) U.S. Cl.
CPC ......... *G01N 33/0098* (2013.01); *A01M 21/00* (2013.01); *G01J 9/00* (2013.01); *G01N 21/255* (2013.01); *H05B 45/10* (2020.01)

(58) Field of Classification Search
CPC . H05B 33/0854; A01M 21/043; A01M 21/00; G01N 33/0098; G01N 21/255; G01J 9/00; G01J 2001/4242
See application file for complete search history.

(56) References Cited

U.S. PATENT DOCUMENTS

| | | | |
|---|---|---|---|
| 5,296,702 A * | 3/1994 | Beck | A01M 7/0089 250/226 |
| 5,763,873 A | 6/1998 | Beck et al. | |
| 5,789,741 A | 8/1998 | Kinter et al. | |
| 7,408,145 B2 * | 8/2008 | Holland | G01J 3/10 250/205 |
| 2005/0098713 A1 | 5/2005 | Holland | |
| 2015/0075066 A1* | 3/2015 | Stowe | A01D 34/015 47/1.3 |
| 2017/0339839 A1* | 11/2017 | Carstensen | A01G 22/00 |

FOREIGN PATENT DOCUMENTS

| | | |
|---|---|---|
| WO | 94/02812 A1 | 2/1994 |
| WO | 97/37372 A1 | 10/1997 |
| WO | 98/11587 A2 | 3/1998 |
| WO | 03/010521 A1 | 2/2003 |

OTHER PUBLICATIONS

European Search Report for Application No. 19 203 983.2-1004, dated Mar. 12, 2020, 5 pages.

* cited by examiner

*Primary Examiner* — Michael P LaPage
(74) *Attorney, Agent, or Firm* — Kilpatrick Townsend & Stockton LLP

(57) ABSTRACT

Methods for controlling a plant detection system include determining a target phase delay based on a first phase delay of reflected portions of a first light beam and a second phase delay of reflected portions of a second light beam. A composite light beam comprising the first light beam and the second light beam is emitter towards bare soil, and reflected portions of the composite light beam are detected. An intensity of at least one of the first light beam or the second light beam is adjusted so that a phase delay of the composite light beam is approximately equal to the target phase delay.

17 Claims, 10 Drawing Sheets

TRANSMIT

RECEIVE

CONTROLLING PLANT DETECTION SYSTEMS USING PHASE DELAY ANALYSIS

FIELD OF THE INVENTION

Embodiments described herein relate generally to plant detection systems, and more particularly, to controlling plant detection systems.

BACKGROUND

The spectral reflectance of a plant compared to that of soil can be used to detect the presence of a plant on the ground. This is shown in FIG. 1, which is an exemplary plot illustrating the reflectance versus wavelength of a living plant 1 compared to that of bare soil 2. Due to the differences between the spectral reflectance characteristics, it is possible to differentiate the living plant 1 from the bare soil 2. For example, light beams of two different wavelengths $W_1$, $W_2$ can be transmitted toward the ground, and the intensities of the different wavelengths of scattered light returning from the ground can be compared to determine if there is a plant 1 or just bare soil 2.

Detecting a plant in this manner can be useful to reduce the amount of herbicide required to eradicate weeds in a field. For example, a field may be scanned using light beams of two different wavelengths, and each time the spectral reflectance characteristic of a weed is detected, a valve may be opened to spray herbicide on the weed. A considerable savings in herbicide may be realized since it is not sprayed unnecessarily onto the bare soil.

Improved methods for detecting the presence of plants on the ground are desired.

SUMMARY

Embodiments described herein provide improved systems and methods for detecting the presence of plants on the ground. In accordance with an embodiment, for example, a method for controlling a plant detection system includes determining a phase delay of a composite light beam that includes light at different wavelengths (e.g., $W_1$, $W_2$). The different wavelengths are selected to provide different spectral reflectance characteristics for living plants and bare soil. Because of the different spectral reflectance characteristics, an intensity of reflected light from the composite light beam will change depending on whether it is reflected from a living plant or bare soil. The change in intensity will cause a change in phase delay that can be used to detect the presence of a plant on the ground.

Detection sensitivity can be improved by adjusting intensities of the emitted light beams so that a phase delay of the composite light beam reflected from bare soil is approximately half way between a phase delay of the light beam at the first wavelength $W_1$ and a phase delay of the light beam at the second wavelength $W_2$. With the phase delay of the composite signal adjusted, a plant detection phase delay can be set that is longer than the phase delay of the composite signal. In some embodiments, measured phase delays can be used to determine soil phase delays and plant phase delays, and the plant detection phase delay can be set based on the soil phase delays and the plant phase delays.

Numerous benefits are achieved using embodiments described herein over conventional techniques. Some embodiments, for example, adjust intensities of emitted light beams so that a phase delay of a composite light beam reflected from bare soil is approximately half way between a phase delay of a light beam at a first wavelength and a phase delay of a light beam at a second wavelength. This can improve detection sensitivity. In other embodiments, measured phase delays can be used to determine soil phase delays and plant phase delays, and a plant detection phase delay can be set based on the measured delays. This can provide a plant detection threshold that improves system performance by reducing false detections without negatively impacting sensitivity. Depending on the embodiment, one or more of these features and/or benefits may exist. These and other benefits are described throughout the specification with reference to the appended drawings.

DETAILED DESCRIPTION

Embodiments described herein provide improved methods for controlling plant detection systems. In accordance with an embodiment, for example, a method for controlling a plant detection system includes adjusting an intensity of one or more emitted light beams so that a phase delay of a composite light beam reflected from bare soil is approximately half way between a phase delay of a light beam at a first wavelength and a phase delay of a light beam at a second wavelength. Adjusting the light beams in this manner can improve sensitivity of the plant detection system.

In some embodiments, measured phase delays can be used to determine soil phase delays and plant phase delays. A plant detection phase delay can be set based on the measured phase delays.

Figure 1:
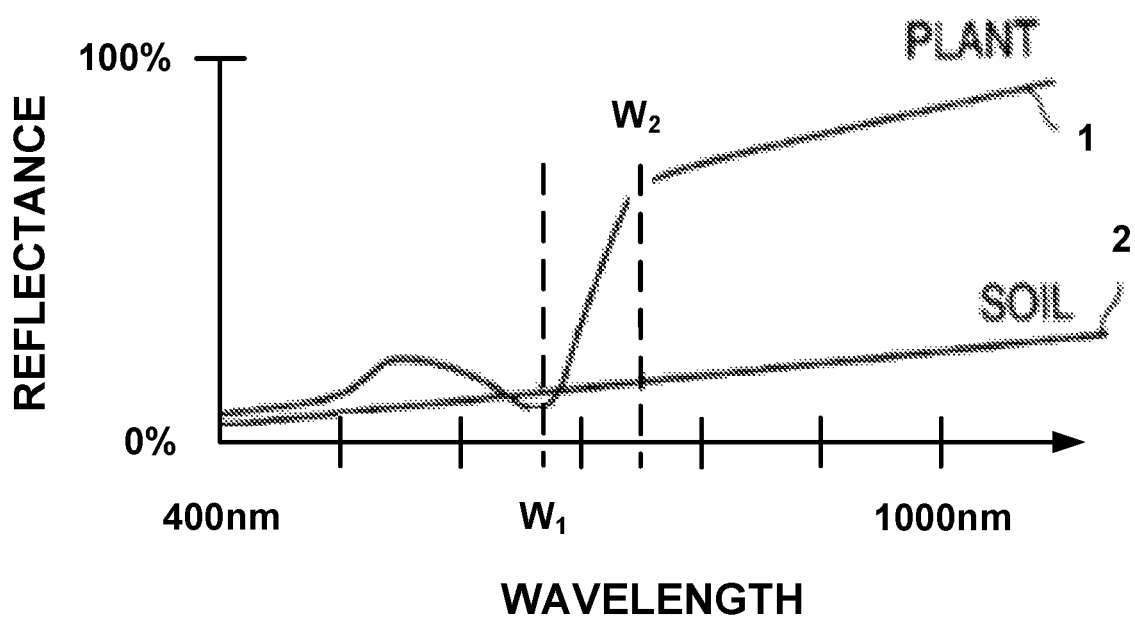
FIG. 1 is a plot illustrating the spectral reflectance of a living plant compared to that of soil.
Figure 2:
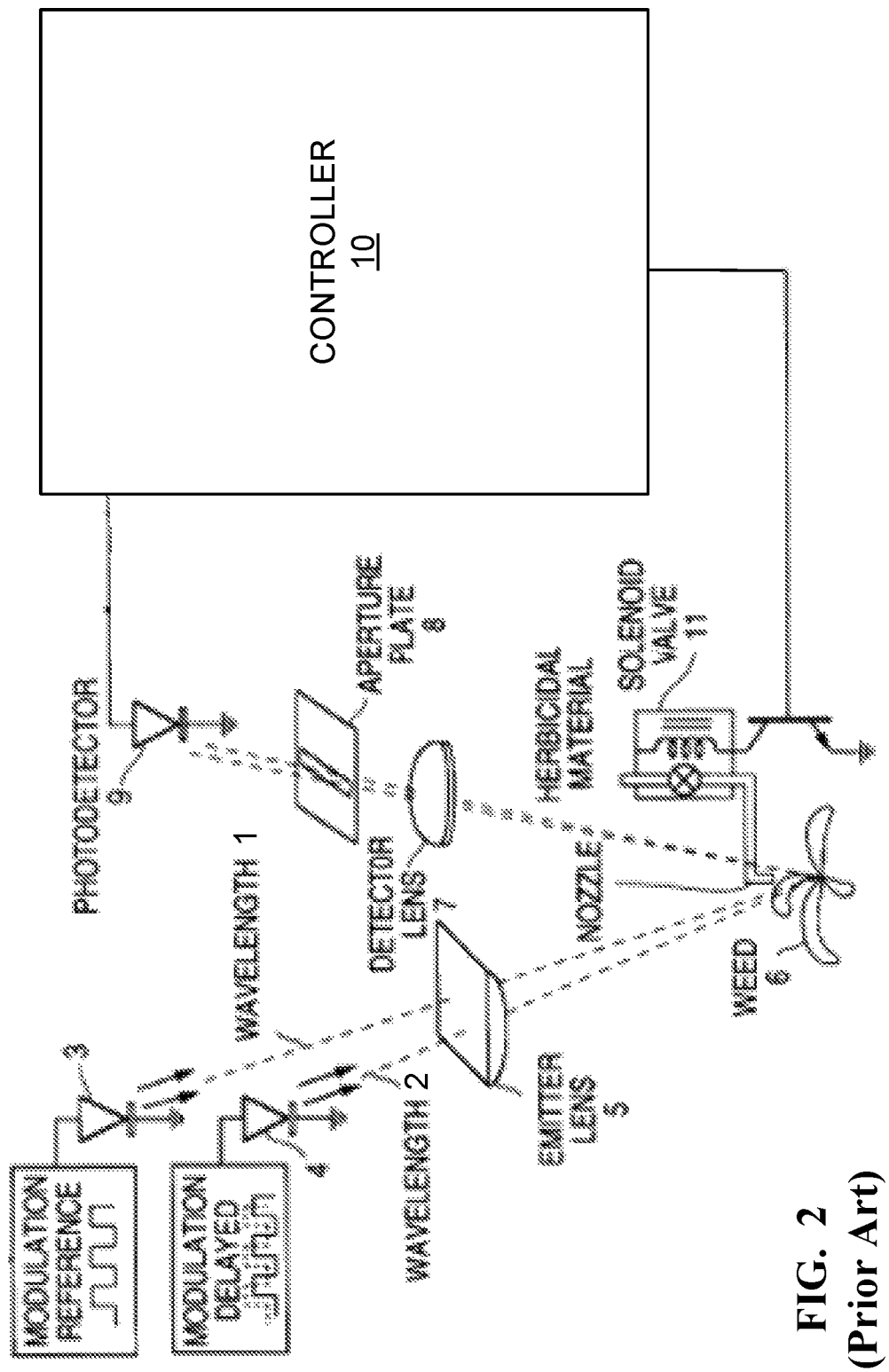
FIG. 2 is a simplified schematic diagram of an exemplary herbicide sprayer system.

FIG. 2 is a simplified schematic diagram of an exemplary herbicide sprayer system that may benefit from the embodiments described herein. The herbicide sprayer system is used merely as an example, and it should be appreciated that the embodiments described herein may be used with other types of plant detection systems.

In the herbicide sprayer system shown in FIG. 2, a first diode 3 emits light at a first wavelength, and a second diode 4 emits light at a second wavelength. In this example, the drive currents of the diodes 3, 4 are each modulated with respective modulation signals that are of the same frequency but different phase. The light from the diodes 3, 4 passes through an emitter lens 5 and is directed toward an object on the ground (in this case a plant 6). Some of the light impinging on the plant 6 is reflected and passes through a detector lens 7 and an aperture plate 8 before impinging on a photodetector 9.

The phase of the scattered light impinging upon the photodetector 9 is used to assess the spectral reflectance characteristics of the reflected light and therefore to characterize the object (e.g., the plant 6 on the ground) from which the light is scattered. For example, if the light from the diode 4 were completely absorbed by the plant 6, then the only light received by the photodetector 9 would be from the diode 3. The photodetector 9 would therefore be modulated with a signal approximately in phase with the modulation signal driving the diode 3.

If, on the other hand, no light from the diode 3 were reflected from the plant 6, then the only light received by the photodetector 9 would be from the diode 4. The photodetector 9 would therefore be modulated with a signal approximately in phase with the modulation signal driving the diode 4.

The foregoing examples represent extreme cases. In practice, the photodetector 9 typically receives some light from each of the diodes 3, 4. Then, depending on the relative reflectance values, the phase of a resonant circuit is between the first and second extreme phase relationships described above.

A phase detector detects the phase of the oscillation providing phase information indicative of the relative strengths of the scattered light beams from the diodes 3, 4. If this phase information is consistent with the spectral reflectance characteristic of a plant 6, then controller 10 provides a signal to open a solenoid valve 11 to spray herbicide onto the plant 6. Conversely, if the phase information is consistent with the spectral reflectance characteristic of soil, the controller 10 does not provide a signal and the solenoid valve 11 remains closed.

It should be appreciated that the schematic diagram shown in FIG. 2 depicts an exemplary herbicide sprayer system. The embodiments described herein are not limited to this system, however, and may be implemented in other systems that may include different and/or additional components.

Figure 3:
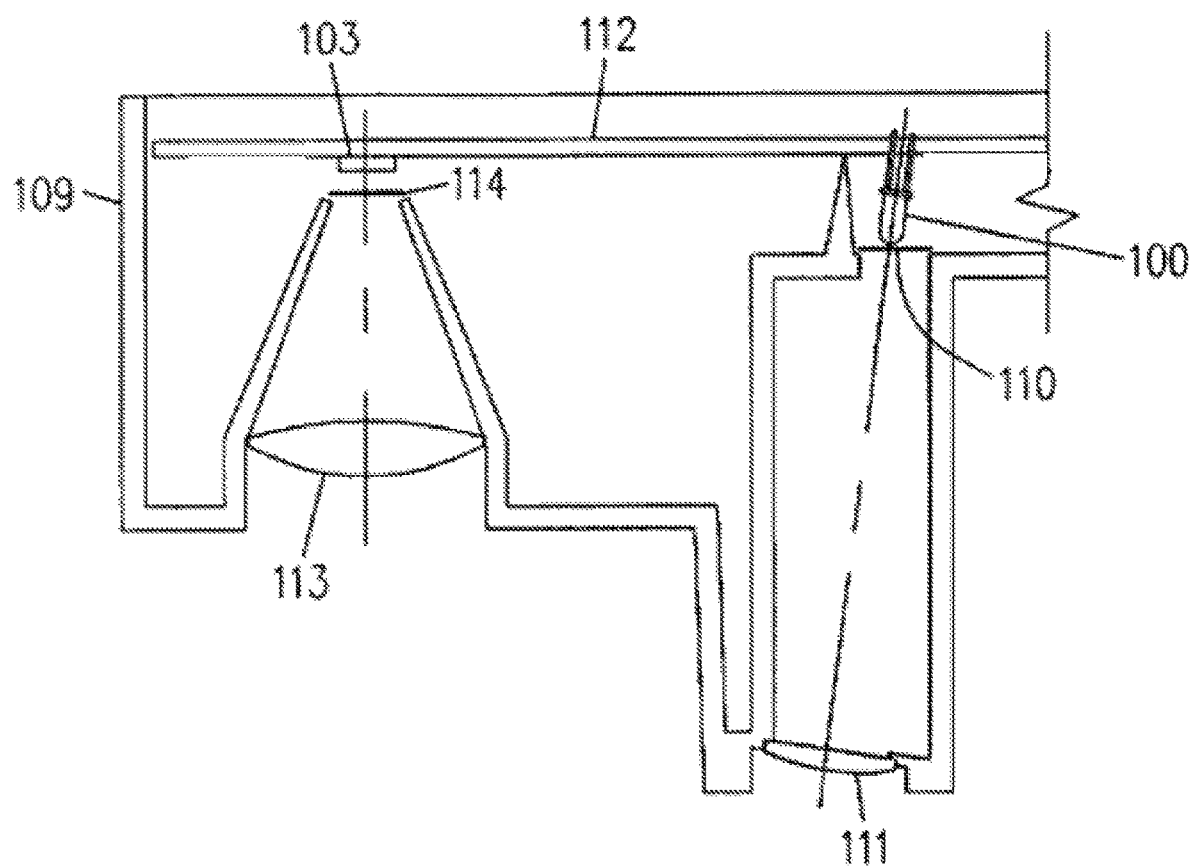
FIG. 3 is a simplified cross-sectional view of a portion of an exemplary herbicide sprayer system.

FIG. 3 is a simplified cross-sectional view of a portion of an exemplary herbicide sprayer system. The portion shown in this figure includes some components for detecting the presence of plants on the ground, such as a housing 109, diodes 100 (e.g., light emitting diodes), an emitter mask 110, an emitter lens 111, a detector lens 113, a detector mask 114, a photodetector 103, and a printed circuit board 112. The emitter mask 110 and/or detector mask 114 may be optional in some embodiments. The diodes 100 may be configured to emit light at different wavelengths as discussed previously (e.g., $W_1$, $W_2$). Portions of the emitted light are reflected by plants and/or bare soil. Reflected portions of the light are received at the photodetector 103, and signals from the photodetector 103 may be used to identify the presence of the plants on the ground.

FIG. 3 does not specifically show all the circuitry and/or hardware components for performing functions such as generating the light, detecting the light, analyzing the spectral reflectance characteristics, and/or controlling valves associated with the sprayer system.

In actual implementations, a plurality of the herbicide sprayer systems may be arranged adjacent to each other on an implement that is coupled to a tractor or another type of farm equipment. The implement is moved back-and-forth across a field to be sprayed. A height of the herbicide sprayer systems above the ground may be adjusted to provide nearly full coverage of the ground under the implement. In some arrangements, the light beams emitted from the herbicide sprayer systems have little to no overlap on the ground to avoid detection and double spraying of plants by adjacent systems.

Figure 4A:
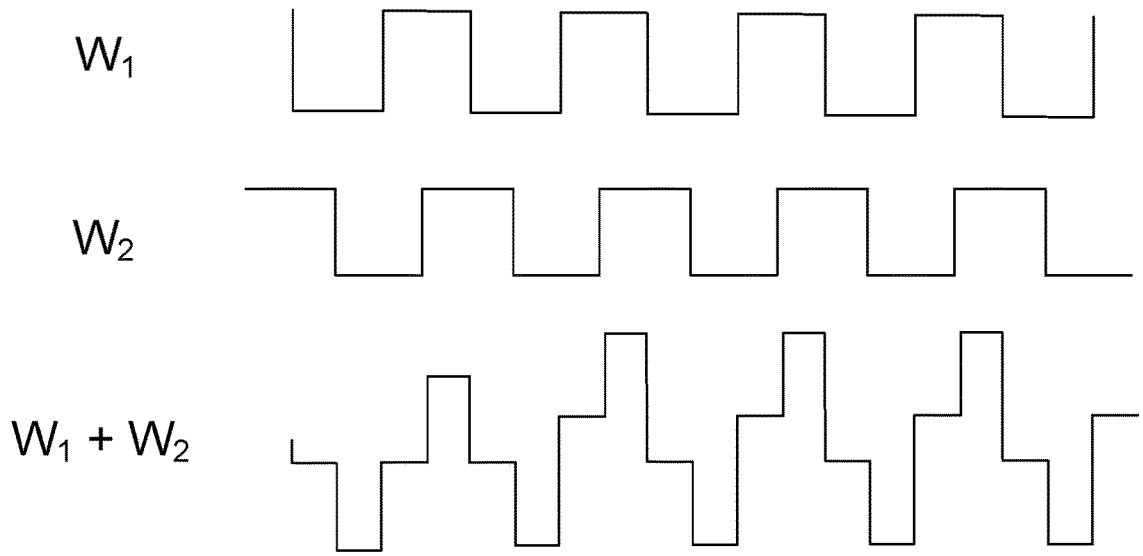
FIGS. 4A-4B are simplified drawings of exemplary signals from a plant detection system.
Figure 4B:
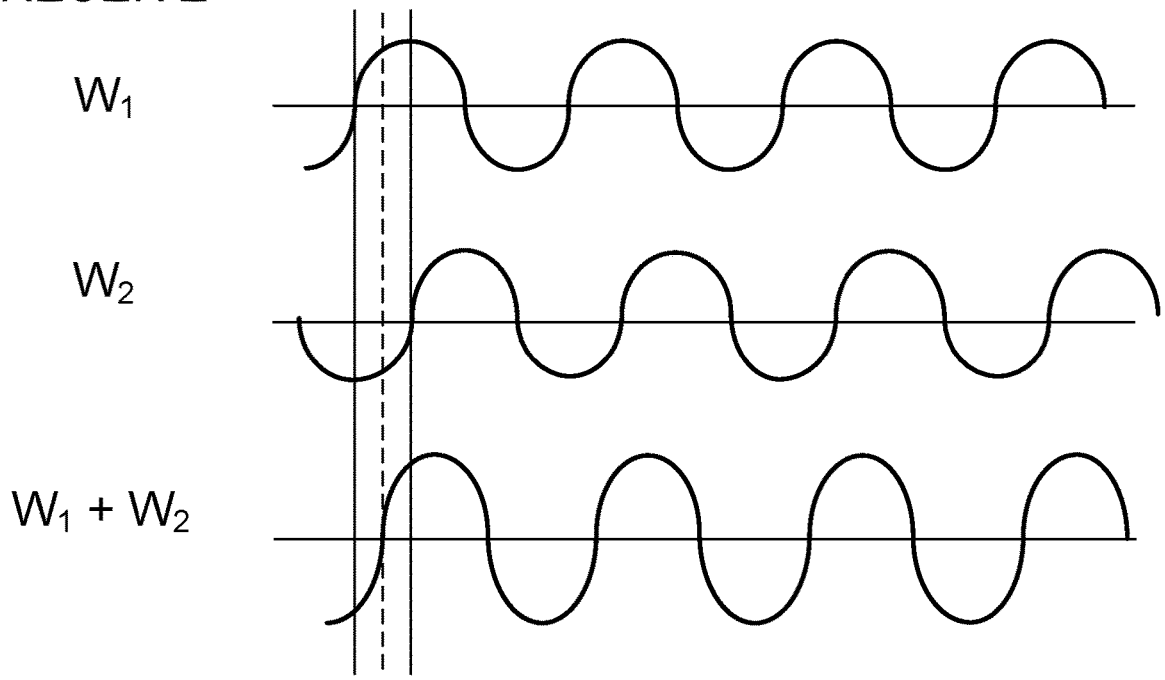

FIGS. 4A-4B are simplified drawings of exemplary signals from a plant detection system. In FIG. 4A, the first signal represents a light beam at a first wavelength $W_1$ that is modulated with a signal having a first phase, and the second signal represents a light beam at a second wavelength $W_2$ that is modulated with a signal having a second phase. As can be seen in this figure, the first phase of the light beam at the first wavelength $W_1$ overlaps with but is shifted from the second phase of the light beam at the second wavelength $W_2$. In this example, the light beams are about 90° out of phase.

The first and second signals are shown for illustrative purposes, but the third signal represents an actual emitted light beam that is a composite of the light beam at the first wavelength $W_1$ and the light beam at the second wavelength $W_2$. In a plant detection system, the composite light beam may be emitted from a light source and directed toward the ground. Light at the different wavelengths may be reflected differently as explained previously. Reflected portions of the light beam may be received at a photodetector module.

In FIG. 4B, the first signal represents detected portions of the light beam at the first wavelength $W_1$, and the second signal represents detected portions of the light beam at the second wavelength $W_2$. The detected portions of the light beams are those portions that are reflected from the ground and received by the photodetector module. As can be seen in this figure, the detected light beams are about 90° out of phase and have similar amplitudes. Similar to FIG. 4B, the first and second signals are shown for illustrative purposes, but the third signal represents an actual detected light beam that is a composite of reflected portions of the light beam at the first wavelength $W_1$ and reflected portions of the light beam at the second wavelength $W_2$. A phase of the composite signal is between the phase of the light beam at the first wavelength $W_1$ and a phase of the light beam at the second wavelength $W_2$.

In the example shown in FIG. 4A, the light beam at the first wavelength $W_1$ and the light beam at the second wavelength $W_2$ have approximately equal amplitudes, and in the example shown in FIG. 4B, the detected portions of the light beam at the first wavelength $W_1$ and the detected portions of the light beam at the second wavelength $W_2$ have approximately equal amplitudes. In actual operation of a plant detection system, however, detected light beams may have different intensities and thus different amplitudes. This can be caused by a number of factors. For example, light emitting diodes (LEDs) that produce light beams at different wavelengths often produce light at different intensities, even when drive currents for the LEDs are the same. Also, as explained previously, light beams at different wavelengths may be reflected differently (particularly if the light is reflected from a plant). The light beams may also be reflected differently from different types of soil. Additionally, the reflected portions of the light beams at different wavelengths may be detected and processed differently. Thus, generally, even if drive currents are the same, or even if emitted intensities are the same, detected intensities of light beams at different wavelengths are different.

Figure 5A:
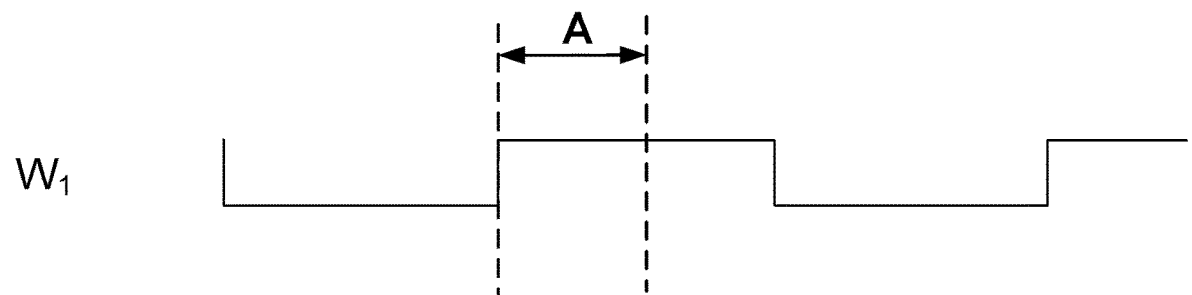
FIGS. 5A-5C and 6A-6B are simplified drawings of exemplary signals from a plant detection system in accordance with some embodiments.
Figure 5B:
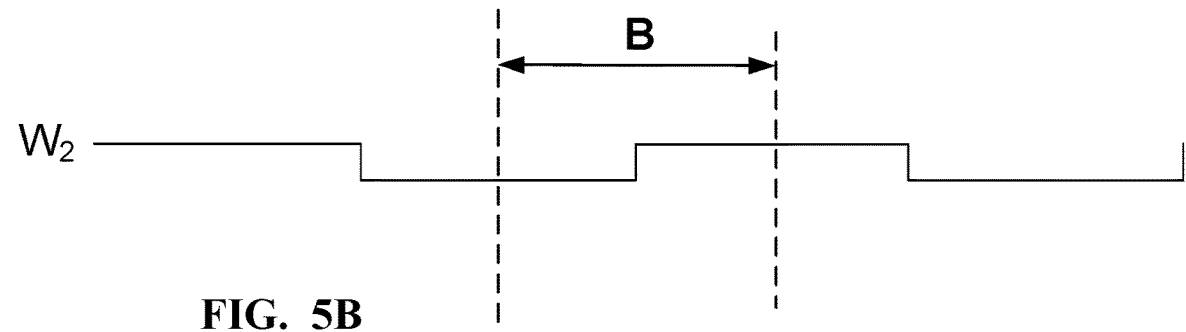
Figure 5C:
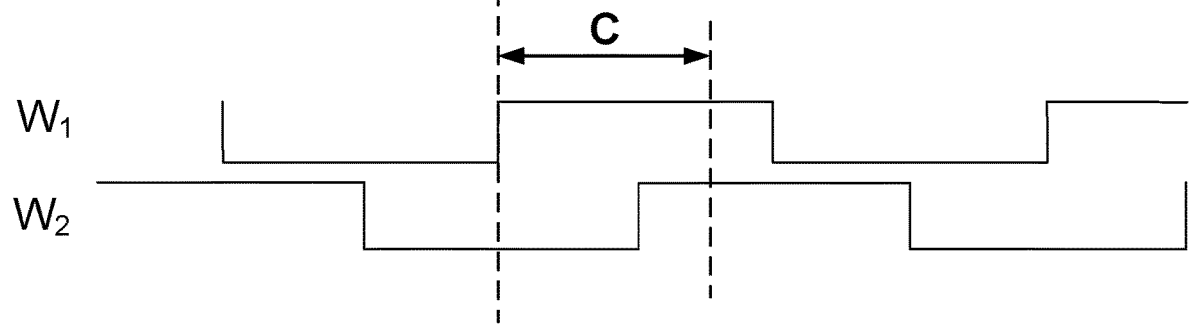

FIGS. 5A-5C are simplified drawings of exemplary signals from a plant detection system in accordance with some embodiments. These figures plot detection signals of a first light beam at a first wavelength $W_1$ and a second light beam at a second wavelength $W_2$. The first light beam is modulated with a first signal having a first phase, and the second light beam is modulated with a second signal having a second phase. The second phase overlaps with but is shifted by about 90° from the first phase.

FIGS. 5A-5C illustrate a calibration process that can be used to determine a target phase delay of a composite light beam to provide maximum detection sensitivity. This occurs when detected portions of the individual light beams that make up the composite light beam have approximately equal amplitudes.

In FIG. 5A, the first light beam at the first wavelength $W_1$ is emitted toward bare soil and reflected portions are detected. A first phase delay (A) is determined. A second light beam at a second wavelength $W_2$ may be turned off while the first phase delay (A) is determined.

In FIG. 5B, the second light beam at the second wavelength $W_2$ is emitted toward the bare soil and reflected portions are detected. A second phase delay (B) is determined. The first light beam at the first wavelength $W_1$ may be turned off while the second phase delay (B) is determined. A target phase delay (C) of a composite signal may be about halfway between the first phase delay (A) and the second phase delay (B).

The phase delays (A), (B), (C) may be determined using a number of different methods. In this example, a point at which a detection signal from the first light beam crosses zero is used as a reference point. The phase delays are values of time between the reference point and a next maximum point of the signal. In other embodiments, the phase delays could be determined based on other signal features. The signals in this example are digitized, but this is not necessary and similar procedures could be used to determine phase delays of analog signals.

In FIG. 5C, a composite light beam comprising light beams at the first wavelength $W_1$ and at the second wavelength $W_2$ is emitted toward the bare soil and reflected portions are detected. An intensity of at least one of the light beams is adjusted so that a phase delay of the composite light beam is approximately equal to the target phase delay (C). This is the point where the first light beam and the second light beam have approximately equal amplitudes.

FIG. 5C illustrates that detected intensities (amplitudes) of the individual light beams are approximately equal and thus the phase delay is approximately equal to the target phase delay (C). In contrast to FIG. 5C, detected amplitude of the first light beam at the first wavelength $W_1$ shown in FIG. 5A is greater than detected amplitude of the second light beam at the second wavelength $W_2$ shown in FIG. 5B. The different amplitudes do not change the phase delay of the individual light beams, however, so the amplitudes can be different while determining the first phase delay (A) and the second phase delay (B). The amplitudes will be approximately equal when the phase delay of the composite signal is approximately equal to the target phase delay (C).

The detected amplitude of the first light beam at the first wavelength $W_1$ (FIG. 5A) and the detected amplitude of the second light beam at the second wavelength $W_2$ (FIG. 5B) does not affect determination of the target phase delay (C). Thus, the target phase delay (C) can be determined over any bare soil. Differences in reflectivity of the individual beams does not change the detected phase delays (A), (B).

Differences in reflectivity can, however, change detected phase delay of the composite signal. Any adjustments to intensities of the individual beams so that the phase delay of the composite signal is approximately equal to the target phase delay (C) are generally made over bare soil that is in or near a field to be sprayed using the plant detection system.

Figure 6A:
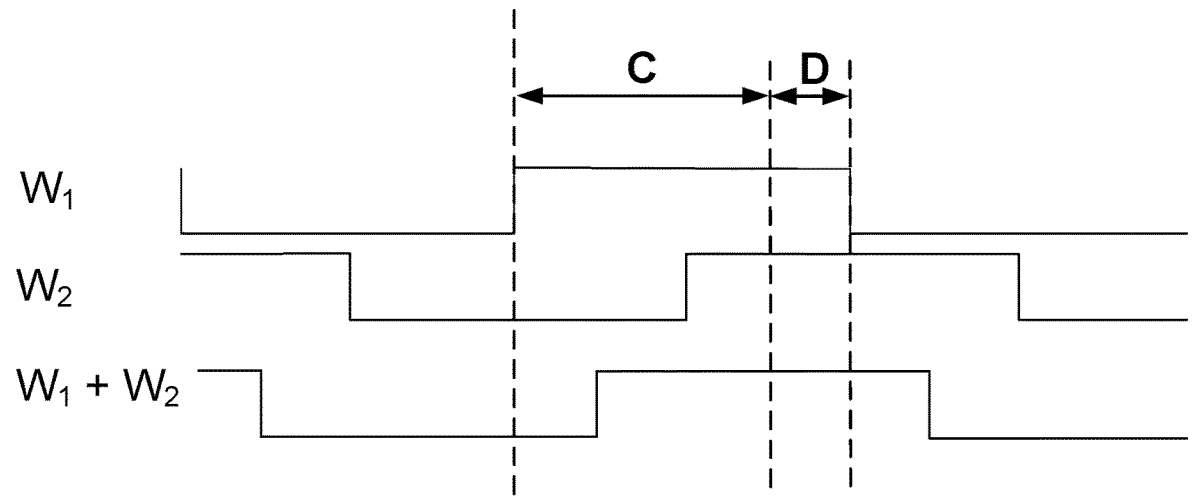
Figure 6B:
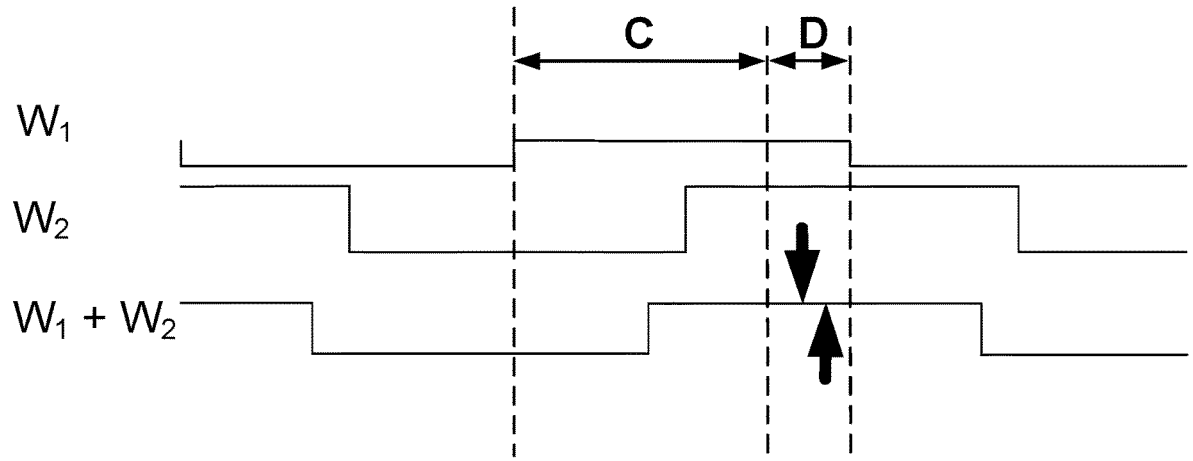

FIGS. 6A-6B are simplified drawings of exemplary signals from a plant detection system in accordance with some embodiments. These figures illustrate a process that can be used to determine a plant detection phase delay. A plant detection phase delay is a threshold phase delay value that falls between a phase delay indicative of a composite light beam reflected off bare soil and a phase delay indicative of a composite light beam reflected off a plant. In some plant detection systems, a signal to open a sprayer valve may be generated when a measured phase delay of the composite light beam is equal to or greater than the plant detection phase delay.

In FIG. 6A, a phase delay of a composite light beam $W_1+W_2$ is approximately equal to the target phase delay (C). This indicates that detected intensities of the first light beam at the first wavelength $W_1$ and the second light beam at the second wavelength $W_2$ are about the same. In this example, a maximum phase delay (C)+(D) is identified. If the composite light beam were directed toward a plant, and the first light beam at the first wavelength $W_1$ were completely absorbed, then the only light received at the photodetector would be from the second light beam at the second wavelength $W_2$, and the phase delay would be (C)+(D).

In FIG. 6B, the target phase delay (C) and the maximum phase delay (C)+(D) are once again shown. In this figure, a detected amplitude of the light beam at the first wavelength $W_1$ is considerably smaller than a detected amplitude of the second light beam at the second wavelength $W_2$. As a result, a phase delay of the composite light beam $W_1+W_2$ is shifted toward the phase delay of the second light beam at the second wavelength $W_2$.

A plant detection phase delay having a longer phase delay than the target phase delay (C) is determined. The plant detection phase delay is longer than the target phase delay (C) but shorter than the maximum phase delay (C)+(D). In this example, the plant detection phase delay is identified by the dark arrow on the left that is pointing downward. A typical phase delay caused by a plant is identified by the dark arrow on the right that is pointing upward. A signal to open a sprayer valve may be generated when a measured phase delay of the composite light beam is equal to or greater than the plant detection phase delay.

Figure 7:
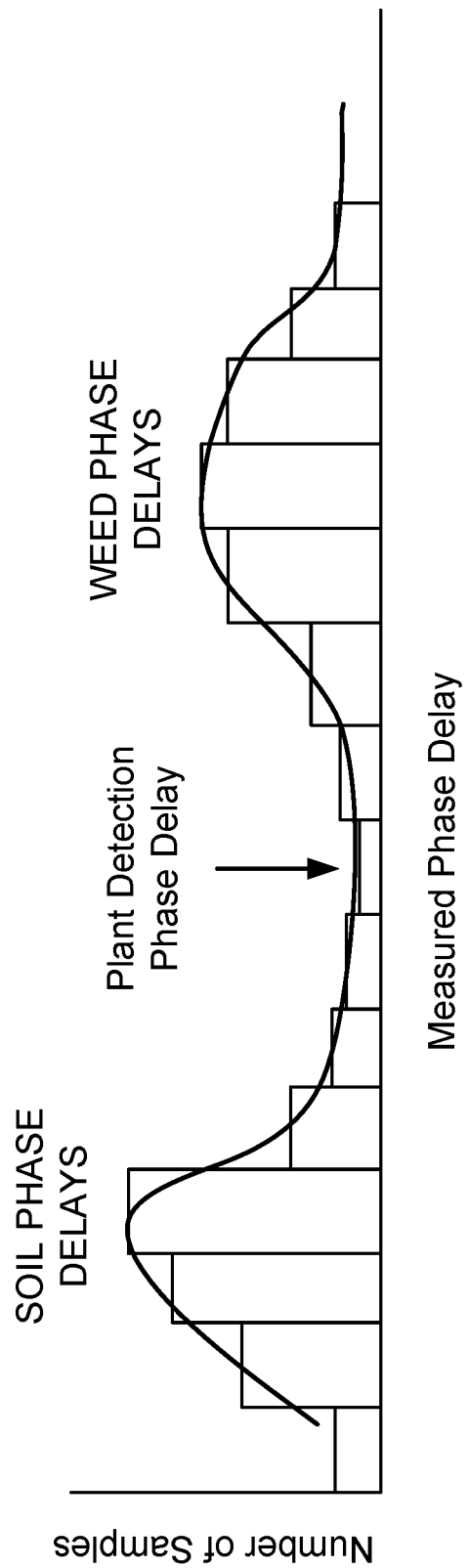
FIG. 7 is a simplified plot of soil phase delays and plant phase delays in accordance with an embodiment.

FIG. 7 is a simplified plot of soil phase delays and plant phase delays in accordance with an embodiment. The data in this plot is exemplary of that obtained from actual measurements of a composite light beam that is scanned across bare soil and plants in a field. Although the plot does not include any units, it represents the number of samples (or measurements) having a particular phase delay. The measured phase delays can be separated into two bins—one for soil phase delays and one for weed phase delays.

In some embodiments, the data from actual measurements can be used to determine a plant detection phase delay. The data may be a snap shot in time that is continuously or periodically updated as additional measurements are performed. The plant detection phase delay can be determined using a number of different methods. For example, the plant detection phase delay may be a delay that is half way between an average of the soil phase delays and an average of the weed phase delays. Alternatively, the plant detection phase delay may be a delay that is half way between a soil phase delay having a maximum number of samples and a weed phase delay having a maximum number of samples. As yet another example, the plant detection phase delay may be the delay between the soil phase delays and the weed phase delays having a minimum number of samples (as shown by the arrow in the plot). Other methods of determining the plant detection phase delay from actual measurements may be used.

Figure 8:
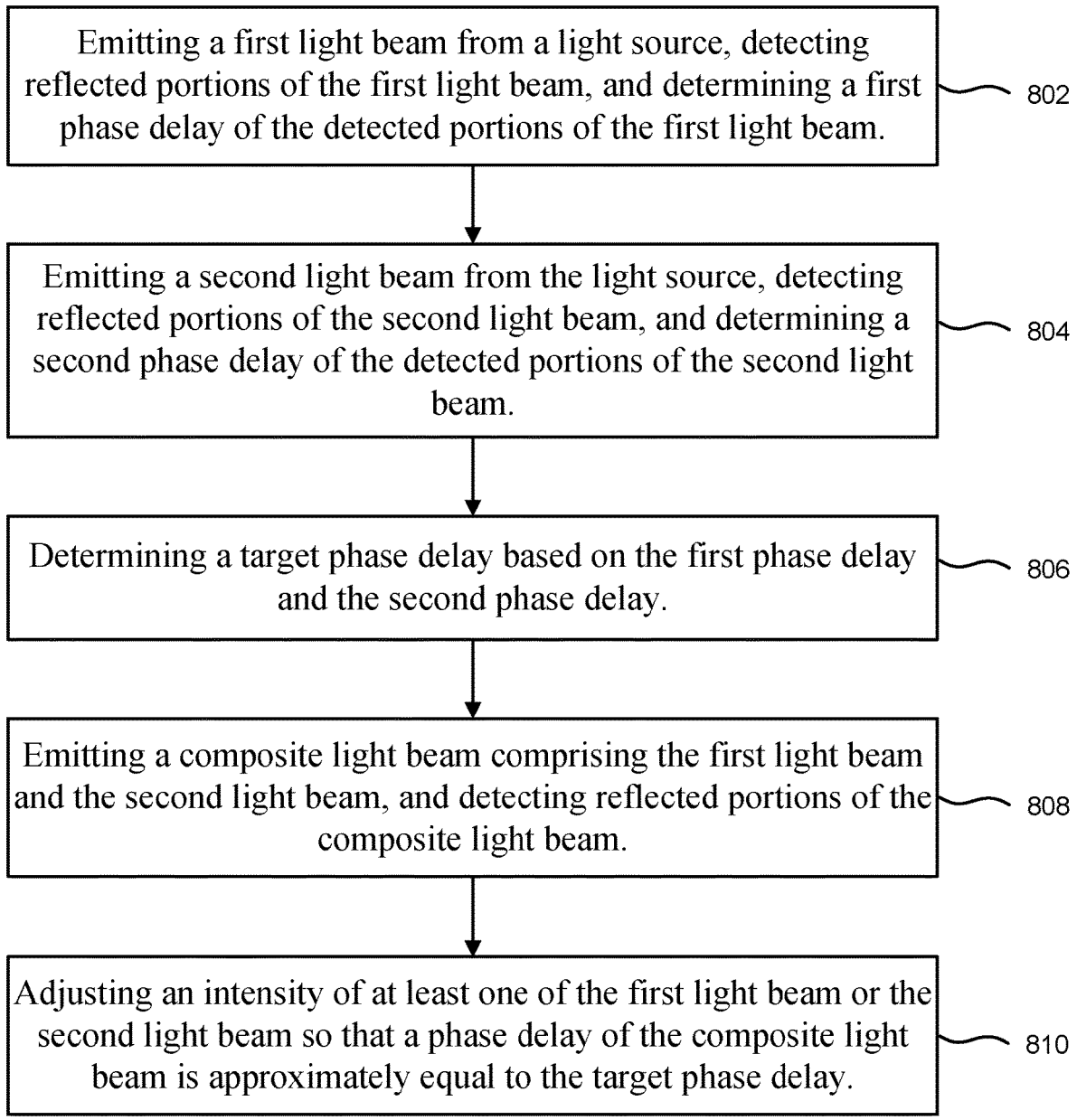
FIGS. 8-10 are flowcharts providing methods for controlling plant detection systems in accordance with some embodiments.

FIG. 8 is a flowchart that provides a method for controlling a plant detection system in accordance with an embodiment. The plant detection system may include a light source and a photodetector module. The light source may be configured to emit a first light beam at a first wavelength and a second light beam at a second wavelength different from the first wavelength. The first light beam may be modulated with a first signal having a first phase, and the second light beam may be modulated with a second signal having a second phase that overlaps with but is shifted from the first phase.

The method illustrated in FIG. 8 may be used to determine a target phase delay of a composite light beam to provide maximum detection sensitivity. The method includes emitting the first light beam from the light source, detecting reflected portions of the first light beam, and determining a first phase delay of the detected portions of the first light beam (802). The first light beam is emitted towards bare soil, and the detected portions of the first light beam are reflected from the bare soil. The reflected portions of the first light beam are detected using the photodetector module. The second light beam may be turned off while the first phase delay is determined. In some embodiments, the first light beam may provide red light at a wavelength of between about 650 nm and 700 nm.

The method includes emitting the second light beam from the light source, detecting reflected portions of the second light beam, and determining a second phase delay of the detected portions of the second light beam (804). The second light beam is emitted towards the bare soil, and the detected portions of the second light beam are reflected from the bare soil. The reflected portions of the second light beam are detected using the photodetector module. The first light beam may be turned off while the second phase delay is determined. In some embodiments, the second light beam may provide near infrared light at a wavelength of greater than about 720 nm.

The method also includes determining a target phase delay based on the first phase delay and the second phase delay (806). In some embodiments, the target phase delay is about halfway between the first phase delay and the second phase delay.

The method also includes emitting a composite light beam comprising the first light beam and the second light beam, and detecting reflected portions of the composite light beam (808). The composite light beam is emitted towards the bare soil, and the detected portions of the composite light beam are reflected from the bare soil. The reflected portions of the composite light beam are detected using the photodetector module.

The method also includes adjusting an intensity of at least one of the first light beam or the second light beam so that a phase delay of the composite light beam is approximately equal to the target phase delay (810). In some embodiments, the intensity of at least one of the first light beam or the second light beam is adjusted by varying a current that drives one or more LEDs associated with either the first light beam or the second light beam.

Figure 9:
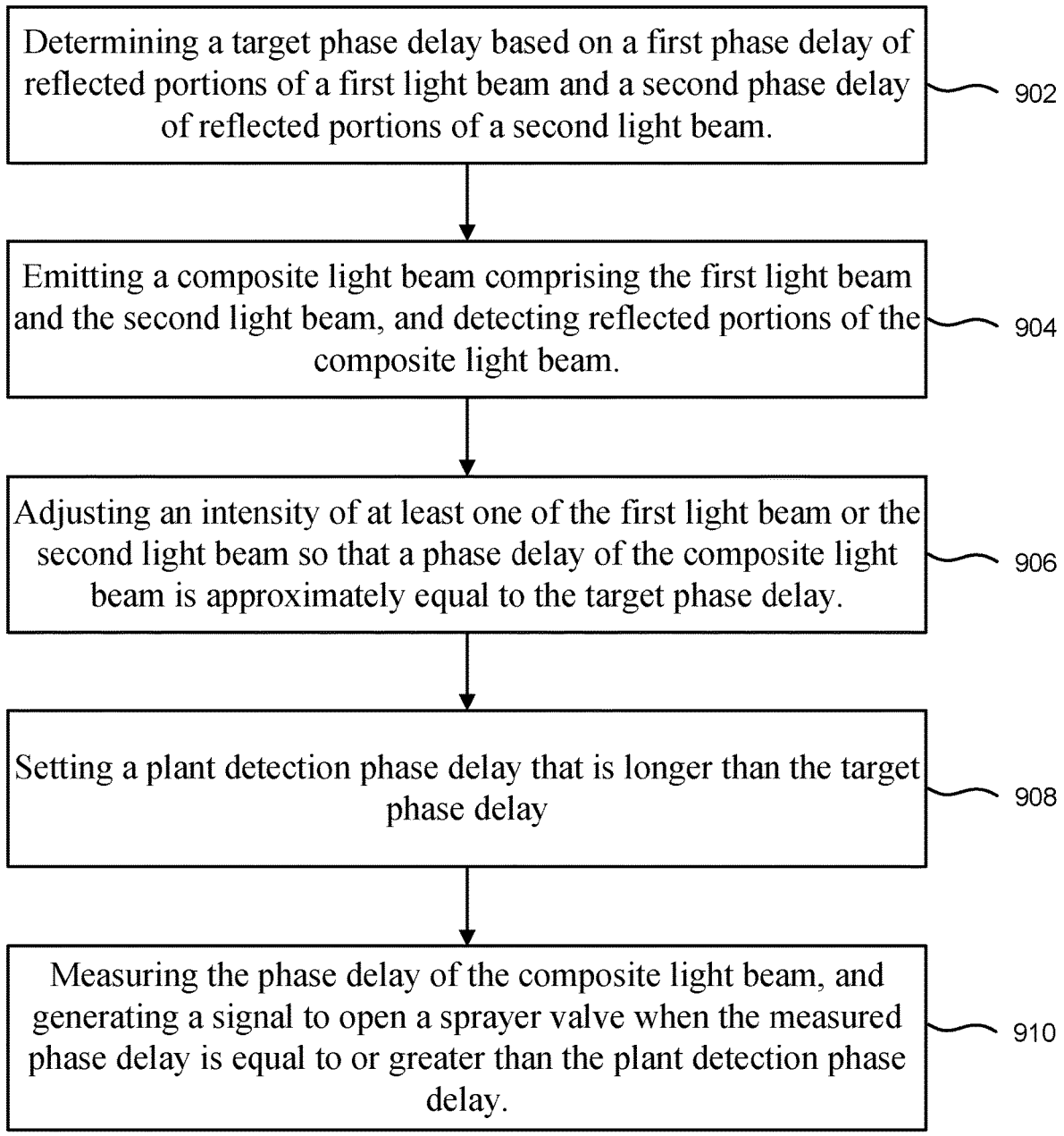

FIG. 9 is a flowchart that provides a method for controlling a plant detection system in accordance with another embodiment. The plant detection system may include a light source and a photodetector module. The light source may be configured to emit a first light beam at a first wavelength and a second light beam at a second wavelength different from the first wavelength. The first light beam may be modulated with a first signal having a first phase, and the second light beam may be modulated with a second signal having a second phase that overlaps with but is shifted from the first phase. In some embodiments, the first phase of the first signal may be shifted by about 90° compared to the second phase of the second signal.

The method illustrated in FIG. 9 may be used to determine a plant detection phase delay. The plant detection phase delay is a threshold value that is associated with detection of a plant. In some plant detection systems, a signal to open a sprayer valve may be generated when a measured phase delay of the composite light beam is equal to or greater than the plant detection phase delay. The method includes determining a target phase delay based on a first phase delay of reflected portions of the first light beam and a second phase delay of reflected portions of the second light beam (902). The reflected portions of the first light beam and the reflected portions of the second light beam are detected using the photodetector module. The target phase delay may be about halfway between the first phase delay and the second phase delay.

The method also includes emitting a composite light beam comprising the first light beam and the second light beam, and detecting reflected portions of the composite light beam (904). The composite light beam is emitted towards bare soil in or near a field to be sprayed using the plant detection system. The reflected portions of the composite light beam are detected using the photodetector module.

The method also includes adjusting an intensity of at least one of the first light beam or the second light beam so that a phase delay of the composite light beam is approximately equal to the target phase delay (906). In some embodiments, the intensity of at least one of the first light beam or the second light beam is adjusted by varying a current that drives LEDs associated with either the first light beam or the second light beam.

The method also includes setting a plant detection phase delay that is longer than the target phase delay (908). The plant detection phase delay is shorter than a maximum phase delay. The maximum phase delay is a delay of the longest one of the first and second phase delays.

The method also includes measuring the phase delay of the composite light beam, and generating a signal to open a sprayer valve when the measured phase delay is equal to or greater than the plant detection phase delay (910). The phase delay of the composite light beam is measured while the composite light beam is moved across the bare soil and plants in the field.

Figure 10:
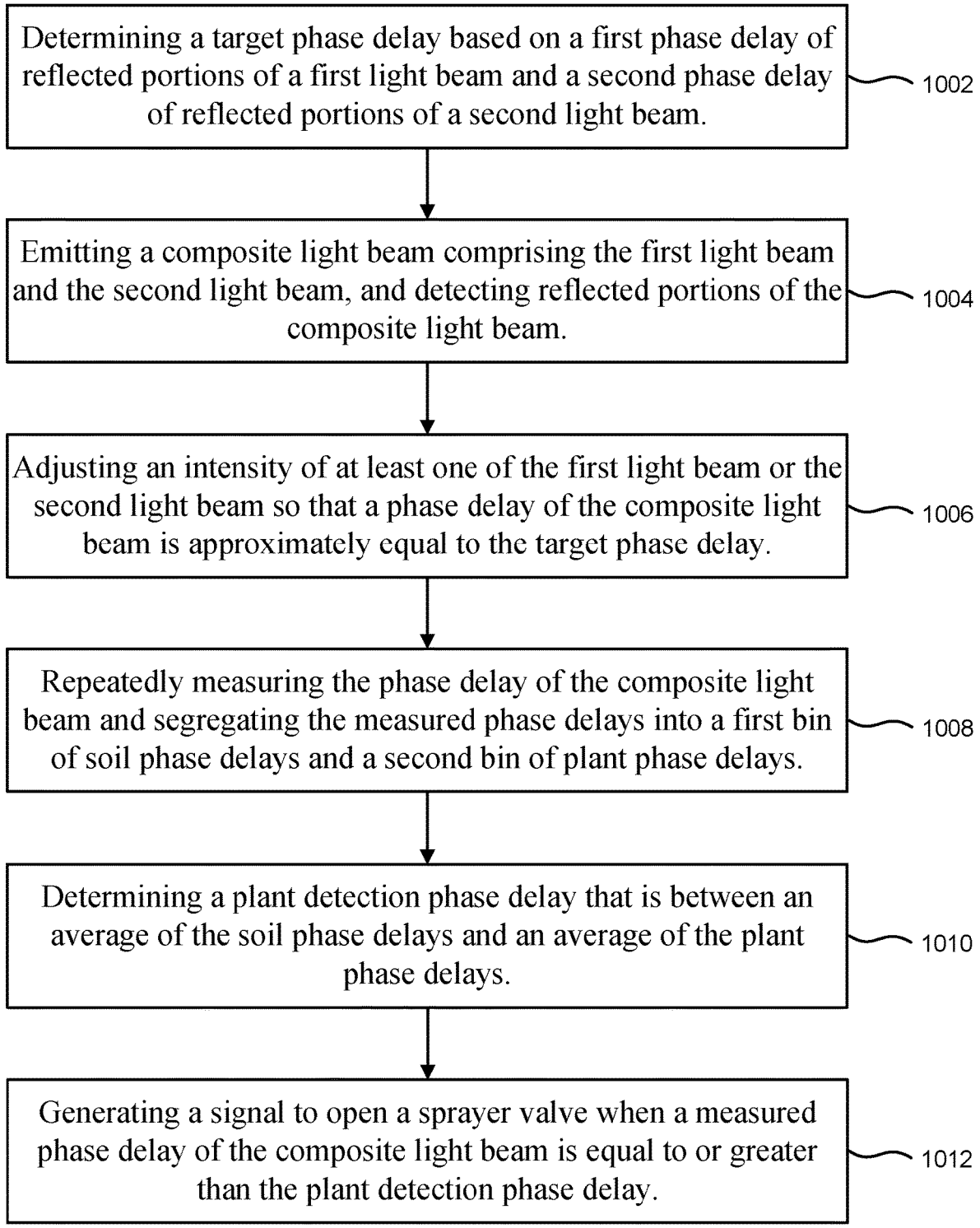

FIG. 10 is a flowchart that provides a method for controlling a plant detection system in accordance with another embodiment. The plant detection system may include a light source and a photodetector module. The light source may be configured to emit a first light beam at a first wavelength and a second light beam at a second wavelength different from the first wavelength. The first light beam may be modulated with a first signal having a first phase, and the second light beam may be modulated with a second signal having a second phase that overlaps with but is shifted from the first phase. In some embodiments, the first phase of the first signal may be shifted by about 90° compared to the second phase of the second signal.

The method illustrated in FIG. 10 may be used to determine a plant detection phase delay. The method includes determining a target phase delay based on a first phase delay of reflected portions of the first light beam and a second phase delay of reflected portions of the second light beam (1002). The reflected portions of the first light beam and the reflected portions of the second light beam are detected using the photodetector module. In some embodiments, the target phase delay is about halfway between the first phase delay and the second phase delay.

The method also includes emitting a composite light beam comprising the first light beam and the second light beam, and detecting reflected portions of the composite light beam (1004). The composite light beam is emitted towards bare soil in or near a field to be sprayed using the plant detection system. The reflected portions of the composite light beam are detected using the photodetector module. In some embodiments, the first light beam provides red light at a wavelength of between about 650 nm and 700 nm, and the second light beam provides near infrared light at a wavelength greater than about 720 nm.

The method also includes adjusting an intensity of at least one of the first light beam or the second light beam so that a phase delay of the composite light beam is approximately equal to the target phase delay (1006). In some embodiments, the intensity of at least one of the first light beam or the second light beam is adjusted by varying a current that drives LEDs associated with either the first light beam or the second light beam.

The method also includes repeatedly measuring the phase delay of the composite light beam, and segregating the measured phase delays into a first bin of soil phase delays and a second bins of plant phase delays (1008). The plant phase delays may be longer than the soil phase delays.

The method also includes determining a plant detection phase delay that is between an average of the soil phase delays and an average of the plant phase delays (1010). The phase delays may be repeatedly measured while the composite light beam is moved or scanned across the bare soil and plants in the field. In some embodiments, the plant detection phase delay is repeatedly determined based on updated values of the soil phase delays and the plant phase delays.

The method also includes generating a signal to open a sprayer valve when a measured phase delay of the composite light beam is equal to or greater than the plant detection phase delay (1012). In some embodiments, the method also includes generating a signal to close the sprayer valve when the measured phase delay of the composite light beam is less than the plant detection phase delay.

It should be appreciated that the specific steps illustrated in FIGS. 8-10 provide particular methods for controlling plant detection systems according to some embodiments of the present invention. Other sequences of steps may also be performed according to alternative embodiments. For example, alternative embodiments may perform the steps outlined above in a different order. Moreover, the individual steps illustrated in FIGS. 8-10 may include multiple sub-steps that may be performed in various sequences. Furthermore, additional steps may be added or removed depending on the particular application.

It should be appreciated that some embodiments may be implemented by hardware, software, firmware, middleware, microcode, hardware description languages, or any combination thereof. When implemented in software, firmware, middleware, or microcode, the program code or code segments to perform the necessary tasks may be stored in a computer-readable medium such as a storage medium. Processors may be adapted to perform the necessary tasks. The term "computer-readable medium" includes, but is not limited to, portable or fixed storage devices, optical storage devices, wireless channels, sim cards, other smart cards, and various other non-transitory mediums capable of storing, containing, or carrying instructions or data.

While the present invention has been described in terms of specific embodiments, it should be apparent to those skilled in the art that the scope of the present invention is not limited to the embodiments described herein. For example, features of one or more embodiments of the invention may be combined with one or more features of other embodiments without departing from the scope of the invention. The specification and drawings are, accordingly, to be regarded in an illustrative rather than a restrictive sense. Thus, the scope of the present invention should be determined not with reference to the above description, but should be determined with reference to the appended claims along with their full scope of equivalents.

What is claimed is:

1. A method for controlling a plant detection system comprising a light source and a photodetector module, the light source configured to emit a first light beam at a first wavelength and a second light beam at a second wavelength different from the first wavelength, the first light beam modulated with a first signal having a first phase, and the second light beam modulated with a second signal having a second phase that overlaps with but is shifted from the first phase, the method comprising:
    emitting the first light beam from the light source, the first light beam directed towards bare soil;
    detecting portions of the first light beam reflected from the bare soil, the portions of the first light beam detected using the photodetector module;
    determining a first phase delay of the portions of the first light beam detected using the photodetector module;
    emitting the second light beam from the light source, the second light beam directed towards the bare soil;
    detecting portions of the second light beam reflected from the bare soil, the portions of the second light beam detected using the photodetector module;
    determining a second phase delay of the portions of the second light beam detected using the photodetector module;
    determining a target phase shift based on the first phase delay and the second phase delay;
    emitting a composite light beam comprising the first light beam and the second light beam, the composite light beam directed towards the bare soil;
    detecting portions of the composite light beam reflected from the bare soil, the portions of the composite light beam detected using the photodetector module; and
    adjusting an intensity of at least one of the first light beam or the second light beam so that a phase shift of the composite light beam is approximately equal to the target phase shift.

2. The method of claim 1 wherein the target phase shift is halfway between the first phase delay and the second phase delay.

3. The method of claim 1 wherein the second light beam is turned off while the first phase delay is determined, and the first light beam is turned off while the second phase delay is determined.

4. The method of claim 1 wherein the intensity of at least one of the first light beam or the second light beam is adjusted by varying a current that drives the light source that comprises light emitting diodes (LEDs) associated with either the first light beam or the second light beam.

5. The method of claim 1 wherein the first light beam provides red light at a wavelength of between 650 nm and 700 nm, and the second light beam provides near infrared light at a wavelength greater than 720 nm.

6. A non-transitory computer readable medium having instructions for causing a computing device to perform the method recited by claim 1.

7. A method for controlling a plant detection system comprising a light source and a photodetector module, the light source configured to emit a first light beam at a first wavelength and a second light beam at a second wavelength different from the first wavelength, the first light beam modulated with a first signal having a first phase, and the second light beam modulated with a second signal having a second phase that overlaps with but is shifted from the first phase, the method comprising:
- determining a target phase shift based on a first phase delay of reflected portions of the first light beam and a second phase delay of reflected portions of the second light beam, the reflected portions of the first light beam and the reflected portions of the second light beam detected using the photodetector module;
- emitting a composite light beam comprising the first light beam and the second light beam, the composite light beam directed towards bare soil in or near a field to be sprayed using the plant detection system;
- detecting reflected portions of the composite light beam using the photodetector module;
- adjusting an intensity of at least one of the first light beam or the second light beam so that a phase shift of the composite light beam is approximately equal to the target phase shift; thereafter
- setting a plant detection phase delay that is longer than the target phase delay;
- measuring the phase shift of the composite light beam while the composite light beam is moved across the bare soil and plants in the field; and
- generating a signal to open a sprayer valve when the measured phase shift of the composite light beam is equal to or greater than the plant detection phase delay.

8. The method of claim 7 wherein the target phase shift is halfway between the first phase delay and the second phase delay.

9. The method of claim 7 wherein the intensity of at least one of the first light beam or the second light beam is adjusted by varying a current that drives the light source that comprises light emitting diodes (LEDs) associated with either the first light beam or the second light beam.

10. The method of claim 7 wherein the first phase of the first signal is shifted by 90° compared to the second phase of the second signal.

11. A non-transitory computer readable medium having instructions for causing a computing device to perform the method recited by claim 7.

12. A method for controlling a plant detection system comprising a light source and a photodetector module, the light source configured to emit a first light beam at a first wavelength and a second light beam at a second wavelength different from the first wavelength, the first light beam modulated with a first signal having a first phase, and the second light beam modulated with a second signal having a second phase that overlaps with but is shifted from the first phase, the method comprising:
- determining a target phase shift based on a first phase delay of reflected portions of the first light beam and a second phase delay of reflected portions of the second light beam, the reflected portions of the first light beam and the reflected portions of the second light beam detected using the photodetector module;
- emitting a composite light beam comprising the first light beam and the second light beam, the composite light beam directed towards bare soil in or near a field to be sprayed using the plant detection system;
- detecting reflected portions of the composite light beam using the photodetector module;
- adjusting an intensity of at least one of the first light beam or the second light beam so that a phase shift of the composite light beam is approximately equal to the target phase shift;
- repeatedly measuring the phase shift of the composite light beam while the composite light beam is scanned across the bare soil and plants in the field, and segregating the measured phase shifts into a first bin of soil phase delays and a second bins of plant phase delays, wherein the plant phase delays are longer than the soil phase delays;
- determining a plant detection phase delay that is between an average of the soil phase delays and an average of the plant phase delays; and thereafter
- generating a signal to open a sprayer valve when a measured phase delay of the composite light beam is equal to or greater than the plant detection phase delay.

13. The method of claim 12 wherein the intensity of at least one of the first light beam or the second light beam is adjusted by varying a current that drives the light source that comprises light emitting diodes (LEDs) associated with either the first light beam or the second light beam.

14. The method of claim 12 wherein the first light beam provides red light at a wavelength of between 650 nm and 700 nm, and the second light beam provides near infrared light at a wavelength greater than about 720 nm.

15. The method of claim 12 wherein the plant detection phase delay is repeatedly determined based on updated values of the average of the soil phase delays and the average of the plant phase delays.

16. The method of claim 12 further comprising:
- generating a signal to close the sprayer valve when the measured phase delay of the composite light beam is less than the plant detection phase delay.

17. A non-transitory computer readable medium having instructions for causing a computing device to perform the method recited by claim 12.

* * * * *